(12) United States Patent
Pettifer et al.

(10) Patent No.: US 6,726,731 B2
(45) Date of Patent: Apr. 27, 2004

(54) FABRIC TREATMENT COMPOSITION

(75) Inventors: Robert Michael Pettifer, Whitley Bay (GB); Shirley Summers, Holystone (GB); Peter Gerard Gray, Tynemouth (GB)

(73) Assignee: Procter & Gamble Company, Cincinnati, OH (US)

( * ) Notice: Subject to any disclaimer, the term of this patent is extended or adjusted under 35 U.S.C. 154(b) by 174 days.

(21) Appl. No.: 09/894,705

(22) Filed: Jun. 28, 2001

(65) Prior Publication Data

US 2002/0108184 A1 Aug. 15, 2002

(51) Int. Cl.[7] ............... D06P 1/64; D06P 1/60
(52) U.S. Cl. ............ 8/549; 8/524; 8/543; 8/900; 8/901; 8/906; 8/907
(58) Field of Search ............. 8/525, 543, 549, 8/906, 907, 901, 900

(56) References Cited

U.S. PATENT DOCUMENTS

| | | | | |
|---|---|---|---|---|
| 186,485 A | * | 1/1877 | Leigh | |
| 618,208 A | * | 1/1899 | Mendess | |
| 1,324,764 A | * | 12/1919 | Wald | |
| 2,014,007 A | * | 9/1935 | Pailler | |
| 5,476,519 A | * | 12/1995 | Haslop et al. | |
| 5,770,552 A | * | 6/1998 | Bruhnke | |

FOREIGN PATENT DOCUMENTS

| | | |
|---|---|---|
| EP | 0 193053 A2 | 9/1986 |
| FR | 1329730 | 6/1963 |
| WO | WO 99/66019 | 12/1999 |

* cited by examiner

*Primary Examiner*—Margaret Einsmann
(74) *Attorney, Agent, or Firm*—Caroline Wei-Berk; Kim W. Zerby; Steve W. Miller

(57) ABSTRACT

The present invention relates to a fabric treatment composition comprising surfactant, fabric substantive dye and dye auxiliary agent. The fabric treatment composition of the invention can be used to change, refresh or maintain the color of fabric.

20 Claims, No Drawings

FABRIC TREATMENT COMPOSITION

FIELD OF THE INVENTION

The present invention relates to compositions which clean and dye fabric. More specifically, the present invention relates to fabric treatment compositions which comprise surfactant, fabric substantive dye and dye auxiliary agent. The compositions of the present invention are suitable for use in fabric cleaning processes for the simultaneous cleaning and dying of fabrics.

BACKGROUND TO THE INVENTION

It is well known that when a dyed fabric is laundered by current laundry detergent products, one main problem which occurs during the washing process is the loss of colour of the fabric with repeated laundering. Detergent ingredients such as surfactant and bleach, pH and other conditions used in the washing process such as temperature and agitation, all contribute to the problem of colour loss from the fabric. Thus, detergent formulations and conditions of the washing process that are optimal for fabric cleaning are usually detrimental for fabric colour care and cause dyed fabric to loose colour. To overcome this problem, the laundry industry has been moving toward detergents with improved fabric colour care benefits. Typically these detergents are bleach free and some comprise detergent ingredients which help keep the dye bound to the surface of the coloured fabric during the washing process. However, after undergoing repeated washing cycles using these detergents, colour loss from the dyed fabric is observed. Thus, there still remains a need to further improve the fabric colour care benefits provided by laundry detergents, particularly after multi-cycle laundering.

The Inventors have surprisingly found that by adding a fabric substantive dye and a dye auxiliary agent to a detergent composition, a detergent composition is obtained which simultaneously cleans and dyes fabric during the washing process. Coloured fabrics that are washed repeatedly using this detergent composition, do not visibly loose any colour during the washing process. Furthermore, this detergent composition can be used to restore a faded coloured fabric back to its original colour level, or change the colour of a fabric, during the washing process.

The Inventors have also surprisingly found that the fabric dying performance of this detergent composition can be achieved by using a lower amount of fabric substantive dye when the amount of dye auxiliary agent present is increased. Also, the Inventors have surprisingly found that when the fabric substantive dye and dye auxiliary agent are present in the same preformed particle, then the fabric dying performance of the composition is further improved. Furthermore, the Inventors have found that the presence of a cationic polymeric material in the detergent composition further, improves the colour care benefits provided by said composition.

SUMMARY OF THE INVENTION

In one embodiment of the present invention, a fabric treatment composition is provided which comprises (by weight) at least 3% surfactant, from 0.01% to 3% fabric substantive dye and at least 10% dye auxiliary agent.

In another embodiment of the present invention, a process for preparing a fabric treatment composition is provided comprising the steps; (a) premixing a fabric substantive dye and a dye auxiliary agent to form a dye premix; and (b) mixing a surfactant with said dye premix.

In another embodiment of the present invention, the use of a fabric treatment composition to change, refresh or maintain the colour of a fabric is provided.

DETAILED DESCRIPTION OF THE INVENTION

Fabric Substantive Dye

The fabric treatment composition, herein referred to as "composition", comprises from 0.01% to 3%, preferably from 0.01%, or preferably from 0.05%, or preferably from 0.1%, or preferably to 2.5%, or preferably to 2%, or preferably to 1.5%, or preferably to 1%, or preferably to 0.7% or preferably to 0.6% fabric substantive dye, herein referred to as "dye". The dye for use herein does not include compounds such as optical brighteners, photo-bleaches and does not include non-fabric substantive dye such as dye used to colour coloured speckles which are added to detergents for aesthetic reasons and which are not designed to bind fabric such as dyes known under the trade names as PIGMASOL GRUN supplied by BASF, monastral blue supplied by Hays Colours Ltd and cosmenyl blue supplied by Clariant. Preferably said dye is a reactive dye, said reactive dye preferably comprises a chromophore group, a linking group and a leaving group.

The leaving group is defined as the chemical group which leaves the rest of the dye (e.g. the linking group and chromophore group) during the chemical reaction(s) which occur during the fabric dying process. Preferably, the leaving group is covalently bound to the rest of the dye. Without wishing to be bound by theory, the inventors believe that the bond which binds the leaving group to the rest of the dye is broken during the chemical reaction(s) of the fabric dying process, and the leaving group leaves the rest of the dye, for example as a halide anion. Once the leaving group has left the rest of the dye, the rest of the dye can bind to fabric, usually to cellulosic fabric, typically covalently bonding with the chemical groups of the fabric. Preferred leaving groups are halide atoms, especially preferred are chlorine and fluorine atoms.

The chromophore group which is comprised by the dye causes the observed change in colour, i.e. the dying effect, which occurs when said dye binds to the fabric. Any known chromophore group can be comprised by the dye. Preferred chromophore groups are chosen depending on the colour of the fabric that is to be treated by the composition herein.

The linking group is defined as the chemical group which links the leaving group to the chromophore. The linking group is usually chemically bound to the leaving group, typically covalently bound, but it may be ionically bound, to the leaving group. Preferred linking groups are triazine or pyrimidine rings, where the leaving group and chromophore group are usually covalently bound to different carbon atoms of the ring. The linking group is believed to increase the rate at which the leaving group leaves the rest of the dye during the dying process, by increasing the chemical stability of the intermediate dye compound which is formed once the leaving group has left the rest of the dye. Reactive dyes comprising a linking group typically show greater dying capability compared to reactive dyes which do not comprise a linking group.

Preferred dyes for use herein are CIBALAN dyes, CIBACHRON dyes and RECATOFIL dyes, all of which are manufactured by Ciba-Geigy, PROCION dyes manufactured by ICI, DRIMARENE dyes manufactured by Sandoz, and LEVAFIX dyes and VEROFIX dyes, both of which are manufactured by Bayer. Most preferred dyes are DRIMARENE dyes.

Dye Auxiliary Agent

The composition herein comprises at least 10%, preferably from 15%, or from 20%, or from 25% or from 30% or from 35%, to 70%, or to 65%, or to 60%, or to 55%, or to 50%, or to 45% dye auxiliary agent.

The dye auxiliary agent preferably comprises an organic acid or salt thereof, preferably organic acid or salt thereof having a molecular weight of less than 2000, preferably less than 1000 or less than 750 or less than 500. Said dye auxiliary agent preferably comprises a carboxylic acid or salt thereof. A preferred carboxylic acid or salt thereof is citric acid or salt thereof. Preferably the dye auxiliary agent comprises an aromatic carboxylic acid or salt thereof, more preferably a benzoic acid or salt thereof, a substituted-benzoic acid or salt thereof, or a combination thereof, most preferably a benzoic acid, a substituted-benzoic acid, or salts thereof. The dye auxiliary agent preferably comprises an organic acid in the form of a salt, more preferably an alkali salt of an organic acid, more preferably a sodium salt of an organic acid.

The dye auxiliary agent improves the colour benefits provided by compositions comprising a fabric substantive dye, by increasing the rate of dye fixation onto the fabric surface. The colour care benefits provided by the fabric substantive dye composition can then be achieved by a lower amount of fabric substantive dye when the dye auxiliary agent is present in the fabric treatment composition. Without wishing to be bound by theory, it is believed that the dye auxiliary agent interacts with the dye and typically increases the rate at which the leaving group leaves the dye by increasing the chemical stability of the intermediate dye compound which is formed once the leaving group has left the dye. The dye auxiliary agent is also thought to minimise the hydrolysis of the intermediate dye compound by water present in the wash solution.

Surfactant

The composition herein comprises at least 3%, preferably at least 4%, or at least 5%, or at least 7%, or at least 8% surfactant. Preferably, the surfactant herein is a surfactant system which comprises more than one type of surfactant. The Inventors have found that improved colour care benefits are provided by the composition herein when the surfactant system comprises a nonionic surfactant, a cationic surfactant or a mixture thereof. Thus, preferably the surfactant comprises a nonionic surfactant, a cationic surfactant or a mixture thereof, preferably a mixture, even more preferably the surfactant comprises a mixture wherein the weight ratio of nonionic surfactant to cationic surfactant is from 5:1 to 20:1, preferably from 6:1, or from 7:1, or from 8:1, or from 9:1, to 18:1, or to 16:1 or to 14:1, or to 12:1.

The Inventors have also found that when the composition herein comprises a surfactant system which is free of anionic surfactant, the colour care benefit provided by said composition is further improved. Without wishing to be bound by theory, the Inventors believe that the anionic surfactant interacts with the dye, most probably with the intermediate dye compound which is formed once the leaving group has left the dye, and prevents the dye from binding to and dying the fabric. The term "free of anionic surfactant" used herein, means that no anionic surfactant is deliberately added to the composition herein. The term "deliberately added" does not include the addition of a very minor amount of anionic surfactant which is either an impurity present in the surfactant which is added to the composition herein. Preferably the composition herein comprises less than 5%, more preferably less than 4%, more preferably less than 3%, more preferably less than 2%, more preferably less than 1%, more preferably less than 0.1%, more preferably less than 0.01% anionic surfactant. Most preferably the composition herein is free of anionic surfactant.

Nonionic Surfactant

The nonionic surfactant which can be used in the present invention are preferably any alkoxylated nonionic surfactant. The ethoxylated and propoxylated nonionic surfactants are preferred. Preferred alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts. Highly preferred are nonionic alkoxylated alcohol surfactants, being the condensation products of aliphatic alcohols with an average of from 1 to 75 moles of alkylene oxide, preferably from 1 to 50 or from 1 to 15 moles, preferably to 11 moles, particularly ethylene oxide and/or propylene oxide, are highly preferred nonionic surfactant comprised in the anhydrous component of the particles of the invention. The alkyl chain of the aliphatic alcohol can either be straight or branched, primary or secondary, and generally contains an average of from 6 to 22 carbon atoms. Particularly preferred are the condensation products of alcohols having an alkyl group containing an average of from 8 to 20, preferably from 12 to 18 carbon atoms with an average of from 2 to 9 moles and in particular an average of 3, 5 or 7 moles, of ethylene oxide per mole of alcohol.

The nonionic surfactant which can be used in the present invention may also comprise polyhydroxy fatty acid amides, in particular those having the structural formula $R^2CONR^1Z$ wherein: R1 is H, $C_{1-18}$, preferably $C_1$–$C_4$ hydrocarbyl, 2-hydroxy ethyl, 2-hydroxy propyl, ethoxy, propoxy, or a mixture thereof, preferable C1–C4 alkyl, more preferably $C_1$ or $C_2$ alkyl, most preferably $C_1$ alkyl (i.e., methyl); and $R_2$ is a $C_5$–$C_{31}$ hydrocarbyl, preferably straight-chain $C_5$–$C_{19}$ or $C_7$–$C_{19}$ alkyl or alkenyl, more preferably straight-chain $C_9$–$C_{17}$ alkyl or alkenyl, most preferably straight-chain $C_{11}$–$C_{17}$ alkyl or alkenyl, or mixture thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl. A preferred nonionic polyhydroxy fatty acid amide surfactant for use herein is a $C_{12}$–$C_{14}$, a $C_{15}$–$C_{17}$ and/or $C_{16}$–$C_{18}$ alkyl N-methyl glucamide. It may be particularly preferred that the composition herein comprises a mixture of a $C_{12}$–$C_{18}$ alkyl N-methyl glucamide and condensation products of an alcohol having an alkyl group containing an average of from 8 to 20 carbon atoms with an average of from 2 to 9 moles and in particular an average of 3, 5 or 7 moles, of ethylene oxide per mole of alcohol. The polyhydroxy fatty acid amide can be prepared by any suitable process. One particularly preferred process is described in detail in WO 9206984. A product comprising about 95% by weight polyhydroxy fatty acid amide, low levels of undesired impurities such as fatty acid esters and cyclic amides, and which is molten typically above about 80° C., can be made by this process.

The nonionic surfactant for use in the present invention may also comprise a fatty acid amide surfactant or alkoxylated fatty acid amide. They include those nonionic surfactants having the formula: $R^6CON(R^7)(R^8)$ wherein $R^6$ is an alkyl group containing from 7 to 21, preferably from 9 to 17 carbon or even 11 to 13 carbon atoms and $R^7$ and $R^8$ are each individually selected from the group consisting of hydrogen, $C_1$–$C_4$ alkyl, $C_1$–$C_4$ hydroxyalkyl, and —$(C_2H_4O)_xH$, where x is in the range of from 1 to 11, preferably 1 to 7, whereby it may be preferred that $R^7$ is different to $R^8$, one having x being 1 or 2, one having x being from 3 to 11 or preferably from 3 to 7.

The nonionic surfactant for use in the present invention may also comprise an alkyl ester of a fatty acid. These nonionic surfactants include those having the formula: $R^9COO(R^{10})$ wherein $R^9$ is an alkyl group containing from 7 to 21, preferably from 9 to 17 carbon or even 11 to 13 carbon atoms and $R^{10}$ is a $C_1$–$C_4$ alkyl, $C_1$–$C_4$ hydroxyalkyl, or —$(C_2H_4O)_xH$, where x is in the range of from 1 to 11, preferably from 1 to 7, more preferably from 1 to 5, whereby it may be preferred that $R^{10}$ is a methyl or ethyl group.

The nonionic surfactant for use in the present invention may also comprise an alkylpolysaccharide, such as those disclosed in U.S. Pat. No. 4,565,647, Llenado, issued Jan. 21, 1986, having a hydrophobic group containing from 6 to 30 carbon atoms and a polysaccharide, e.g., a polyglycoside, hydrophilic group containing from 1.3 to 10 saccharide units.

Preferred alkylpolyglycosides have the formula

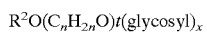

$R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl is preferably derived from glucose.

Cationic Surfactant

The cationic surfactant for use in the present invention preferably comprises a cationic ester surfactant, a cationic mono-alkoxylated amine surfactant, a cationic bis-alkoxylated amine surfactant or a mixture thereof.

The cationic mono-alkoxylated amine surfactant for use herein, has the general formula:

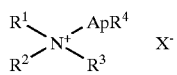

wherein $R^1$ is an alkyl or alkenyl moiety containing from about 6 to about 24 carbon atoms; $R^2$ and $R^3$ are each independently alkyl groups containing from one to about three carbon atoms, preferably methyl; $R^4$ is selected from hydrogen (preferred), methyl and ethyl, $X^-$ is an anion such as chloride, bromide, methylsulphate, sulphate, or the like, to provide electrical neutrality; A is selected from $C_1$–$C_4$ alkoxy, especially ethoxy (i.e., —$CH_2CH_2O$—), propoxy, butoxy and mixtures thereof; and p is from 1 to about 30, preferably 1 to about 15, most preferably 1 to about 8.

Highly preferred cationic mono-alkoxylated amine surfactants for use herein are of the formula:

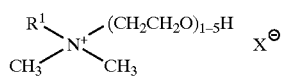

wherein $R^1$ is $C_6$–$C_{24}$ hydrocarbyl and mixtures thereof, preferably $C_6$–$C_{18}$, especially $C_6$–$C_{14}$ alkyl, and X is any convenient anion to provide charge balance, preferably chloride or bromide.

As noted, compounds of the foregoing type include those wherein the ethoxy ($CH_2CH_2O$) units (EO) are replaced by butoxy, isopropoxy [$CH(CH_3)CH_2O$] and [$CH_2CH(CH_3O$] units (i-Pr) or n-propoxy units (Pr), or mixtures of EO and/or Pr and/or i-Pr units.

The cationic bis-alkoxylated amine surfactant for use herein, has the general formula:

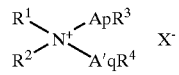

wherein $R^1$ is an alkyl or alkenyl moiety containing from about 6 to about 124 carbon atoms, preferably 6 to about 18 carbon atoms, more preferably 6 to about 16 carbon atoms; $R^2$ is an alkyl group containing from one to three carbon atoms, preferably methyl; $R^3$ and $R^4$ can vary independently and are selected from hydrogen (preferred), methyl and ethyl, $X^-$ is an anion such as chloride, bromide, methylsulphate, sulphate, or the like, sufficient to provide electrical neutrality. A and A' can vary independently and are each selected from $C_1$–$C_4$ alkoxy, especially ethoxy, (i.e., —$CH_2CH_2O$—), propoxy, butoxy and mixtures thereof; p is from 1 to about 30, preferably 1 to about 4 and q is from 1 to about 30, preferably 1 to about 4, and most preferably both p and q are 1.

Highly preferred cationic bis-alkoxylated amine surfactants for use herein are of the formula:

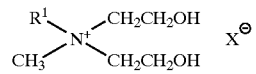

wherein $R^1$ is $C_6$–$C_{24}$ hydrocarbyl and mixtures thereof, preferably $C_6$, $C_8$, $C_{10}$, $C_{12}$ or $C_{14}$ alkyl and mixtures thereof. X is any convenient anion to provide charge balance, preferably chloride. With reference to the general cationic bis-alkoxylated amine structure noted above, since in a preferred compound $R^1$ is derived from (coconut $C_{12}$–$C_{14}$ alkyl fraction fatty acids, $R^2$ is methyl and $ApR^3$ and $A'qR^4$ are each monoethoxy.

Another cationic bis-alkoxylated amine surfactant for use herein includes compounds of the formula:

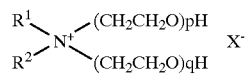

wherein $R^1$ is $C_6$–$C_{18}$ hydrocarbyl, preferably $C_6$–$C_{14}$ alkyl, independently p is 1 to about 3 and q is 1 to about 3, $R^2$ is $C_1$–$C_3$ alkyl, preferably methyl, and X is an anion, especially chloride or bromide. Other compounds of the foregoing type include those wherein the ethoxy ($CH_2CH_2O$) units (EO) are replaced by butoxy (Bu) isopropoxy [$CH(CH_3)CH_2O$] and [$CH_2CH(CH_3O$] units (i-Pr) or n-propoxy units (Pr), or mixtures of EO and/or Pr and/or i-Pr units.

Anionic Surfactant

For the reasons mentioned above, preferably the composition herein is free of anionic surfactant. In certain circumstances, the composition herein may comprise an anionic surfactant. For example, the surfactant for use in the present invention may comprise any anionic surfactant useful for detersive purposes. Examples include salts (including, for example, sodium, potassium, ammonium, and substituted ammonium salts such as mono-, di- and triethanolamine salts) of the anionic sulphate, sulphonate, carboxylate and sarcosinate surfactants. Anionic sulphate surfactants are typically used. Other anionic surfactants include the isethionates such as the acyl isethionates, N-acyl taurates, fatty acid amides of methyl tauride, alkyl succinates and sulfosuccinates, monoesters of sulfosuccinate (especially saturated and unsaturated $C_{12}$–$C_{18}$ monoesters)

diesters of sulfosuccinate (especially saturated and unsaturated $C_6$–$C_{14}$ diesters), N-acyl sarcosinates. Resin acids and hydrogenated resin acids may also be used, such as rosin, hydrogenated rosin, and resin acids and hydrogenated resin acids present in or derived from tallow oil.

Anionic sulphate surfactants which may be used herein include the linear and branched primary and secondary alkyl sulphates, alkyl ethoxysulphates, fatty oleoyl glycerol sulphates, alkyl phenol ethylene oxide ether sulphates, the $C_5$–$C_{17}$ acyl-N-($C_1$–$C_4$ alkyl) and —N-($C_1$–$C_2$ hydroxyalkyl) glucamine sulphates, and sulphates of alkylpolysaccharides such as the sulphates of alkylpolyglucoside (the nonionic non-sulphated compounds being described herein).

Alkyl sulphate surfactants are typically selected from the linear and branched primary $C_9$–$C_{22}$ alkyl sulphates, more preferably the $C_{11}$–$C_{15}$ branched chain alkyl sulphates and the $C_{12}$–$C_{14}$ linear chain alkyl sulphates. Alkyl ethoxysulfate surfactants are typically selected from the group consisting of the $C_{10}$–$C_{18}$ alkyl sulphates which have been ethoxylated with from 0.5 to 50 moles of ethylene oxide per molecule. Usually, the alkyl ethoxysulfate surfactant is a $C_{11}$–$C_{18}$, typically a $C_{11}$–$C_{15}$ alkyl sulphate which has been ethoxylated with from 0.5 to 7, usually from 1 to 5, moles of ethylene oxide per molecule.

Anionic sulphonate surfactants which may be used herein include the salts of $C_5$–$C_{20}$ linear or branched alkylbenzene sulphonates, alkyl ester sulphonates, in particular methyl ester sulphonates, $C_6$–$C_{22}$ primary or secondary alkane sulphonates, $C_6$–$C_{24}$ olefin sulphonates, sulphonated polycarboxylic acids, alkyl glycerol sulphonates, fatty acyl glycerol sulphonates, fatty oleyl glycerol sulphonates, and any mixtures thereof.

Anionic carboxylate surfactants which may be used herein include the alkyl ethoxy carboxylates, the alkyl polyethoxy polycarboxylate surfactants and the soaps ('alkyl carboxyls'), especially certain secondary soaps as described herein. Typical alkyl ethoxy carboxylates which may be used herein include those with the formula $RO(CH_2CH_2O)_x CH_2COO^-M^+$ wherein R is a $C_6$ to $C_{18}$ alkyl group, x ranges from 0 to 10, and the ethoxylate distribution is such that, on a weight basis, the amount of material where x is 0 is less than 20% and M is a cation. Typical alkyl polyethoxy polycarboxylate surfactants which may be used herein include those having the formula RO—($CHR_1$—$CHR_2$—O)$_x$—$R_3$ wherein R is a $C_6$ to $C_{18}$ alkyl group, x is from 1 to 25, $R_1$ and $R_2$ are selected from the group consisting of hydrogen, methyl acid radical, succinic acid radical, hydroxysuccinic acid radical, and mixtures thereof, and $R_3$ is selected from the group consisting of hydrogen, substituted or unsubstituted hydrocarbon having between 1 and 8 carbon atoms, and mixtures thereof. Typical soap surfactants which may be used herein include the secondary soap surfactants which contain a carboxyl unit connected to a secondary carbon. Usually, secondary soap surfactants which may be used herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressers.

Other anionic surfactants which may be used herein are the alkali metal sarcosinates of formula R—CON ($R^1$) $CH_2$ COOM, wherein R is a $C_5$–$C_{17}$ linear or branched alkyl or alkenyl group, $R^1$ is a $C_1$–$C_4$ alkyl group and M is an alkali metal ion. Typical examples are the myristyl and oleoyl methyl sarcosinates in the form of their sodium salts.

Amphoteric Surfactant

The composition herein may comprise an amphoteric surfactant. Suitable amphoteric surfactants which may be used herein include amine oxide surfactants and alkyl amphocarboxylic acids. Typical amine oxides include those compounds having the formula $R^3(OR^4)_xN^O(R^5)_2$ wherein $R^3$ is selected from an alkyl, hydroxyalkyl, acylamidopropoyl and alkyl phenyl group, or mixtures thereof, containing from 8 to 26 carbon atoms; $R^4$ is an alkylene or hydroxyalkylene group containing from 2 to 3 carbon atoms, or mixtures thereof; x is from 0 to 5, preferably from 0 to 3; and each $R^5$ is an alkyl or hydroxyalkyl group containing from 1 to 3, or a polyethylene oxide group containing from 1 to 3 ethylene oxide groups. Preferred are $C_{10}$–$C_{18}$ alkyl dimethylamine oxide, and $C_{10-18}$ acylamido alkyl dimethylamine oxide. A typical example of an alkyl amphodicarboxylic acid for use herein is Miranol(TM) C2M Conc. manufactured by Miranol, Inc., Dayton, N.J.

Zwitterionic Surfactant

The composition herein may comprise a zwitterionic surfactant. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine and sultaine surfactants are typical the zwitterionic surfactants which may be used herein. Typical betaines are those compounds having the formula $R(R')_2N^+R^2COO^-$ wherein R is a $C_6$–$C_{18}$ hydrocarbyl group, each $R^1$ is typically $C_1$–$C_3$ alkyl, and $R^2$ is a $C_1$–$C_5$ hydrocarbyl group. More typically, betaines which are $C_{12-18}$ dimethylammonio hexanoate and the $C_{10-18}$ acylamidopropane (or ethane) dimethyl (or diethyl) betaines may be used herein. Complex betaine surfactants may also be used herein.

Cationic Polymeric Material

The composition herein may comprise from 0.1% to 10%, preferably from 0.2%, or from 0.5%, or from 1%, to 9%, or to 7%, or to 5%, or to 4% or to 3% cationic polymeric material. Preferably the cationic polymeric material is a water-soluble cationic compound which is selected from the group consisting of cationic mono- di- and polyamines.

The cationic polymeric material herein is preferably selected from the group consisting of;

1. ethoxylated cationic diamines having the formula

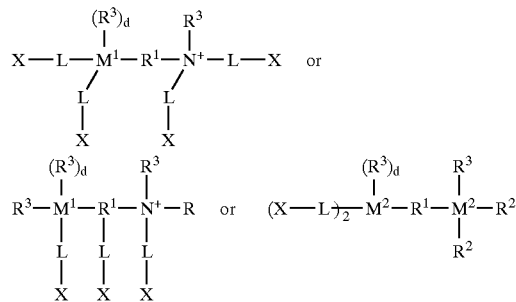

wherein $M^1$ is an N+ or N group; each $M^2$ is an N+ or N group, and at least one $M^2$ is an N+ group; and 2. ethoxylated cationic polyamines having the formula

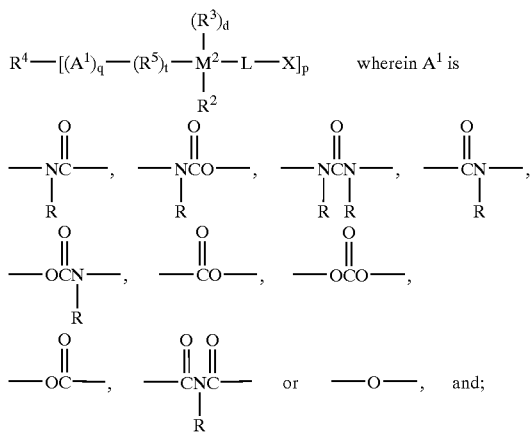

3. mixtures thereof;
wherein, R is H or $C_1$–$C_4$ alkyl or hydroxyalkyl, $R^1$ is $C_2$–$C_{12}$ alkylene, hydroxyalkylene, alkenylene, arylene or alkarylene, or a $C_2$–$C_3$ oxyalkylene moiety having from 2 to about 20 oxyalkylene units provided that no O—N bonds are formed; each $R^2$ is $C_1$–$C_4$ alkyl or hydroxyalkyl, the moiety —L—X, or two $R^2$ together form the moiety —$(CH_2)_r$—$A^2$—$(CH_2)_s$—, wherein $A^2$ is —O— or —$CH_2$—, r is 1 or 2, s is 1 or 2 and r+s is 3 or 4; each $R^3$ is $C_1$–$C_8$ alkyl or hydroxyalkyl, benzyl, the moiety L—X, or two $R^3$ or one $R^2$ and one $R^3$ together form the moiety —$(CH_2)_r$—$A^2$—$(CH_2)_s$—; $R^4$ is a substituted $C_3$–$C_{12}$ alkyl, hydroxyalkyl, alkenyl, aryl or alkaryl group having p substitution sites; $R^5$ is $C_1$–$C_{12}$ alkenyl, hydroxyalkylene, alkenylene, arylene or alkarylene, or a $C_2$–$C_3$ oxyalkylene moiety having from 2 to about 20 oxyalkylene units provided that no O—O or O—N bonds are formed; X is a nonionic group selected from the group consisting of H, $C_1$–$C_4$ alkyl or hydroxyalkyl ester or ether groups, and mixtures thereof; L is a hydrophilic chain which contains the polyoxyalkylene moiety —[($R^6$O)$_m$($CH_2CH_2O$)$_n$]—; wherein $R^6$ is $C_3$–$C_4$ alkylene or hydroxyalkylene and m and n are numbers such that the moiety —$(CH_2CH_2O)_n$— comprises at least about 50% by weight of said polyoxyalkylene moiety; d is 1 when $M^2$ is N+ and is 0 when $M^2$ is N; n is at least about 16 for said cationic monoamines, is at least about 6 for said cationic diamines and is at least about 3 for said cationic polyamines; p is from 3 to 8; q is 1 or 0; t is 1 or 0, provided that t is 1 when q is 1; and The cationic polymeric material herein can also comprise ethoxylated cationic diamines and ethoxylated cationic polyamines.

The positive charge of the N+ groups is offset by the appropriate number of counter anions. Suitable counter anions include Cl—, Br—, $SO_3^{-2}$, $PO_4^{-2}$, $MeOSO_3$— and the like. Particularly preferred counter anions are Cl— and Br—.

X can be a non-ionic group selected from hydrogen (H), $C_1$–$C_4$ alkyl or hydroxyalkyl ester or ether groups, or mixtures thereof. Preferred esters or ethers are the acetate ester and methyl ether, respectively. The particularly preferred nonionic groups are H and the methyl ether.

In the preceding formulae, hydrophilic chain L usually consists entirely of the polyoxyalkylene moiety —[($R^6$O)$_m$($CH_2CH_2$-$O_n$)—]. The moieties —($R^6$O)m— and —($CH_2CH_2$O)n— of the polyoxyalkylene moiety can be mixed together or preferably form blocks of —($R^6$O)$_m$— and —$(CH_2CH_2O)_n$— moieties. $R^6$ is preferably $C_3H_6$ (propylene); m is preferably from 0 to about 5 and is most preferably 0, i.e. the polyoxyalkylene moiety consists entirely of the moiety —$(CH_2CH_2O)_n$—. The moiety —$(CH_2CH_2O)_n$— preferably comprises at least about 85% by weight of the polyoxyalkylene moiety and most preferably 100% by weight (m is 0).

In the preceding formulas, $M^1$ and each $M^2$ are preferably an N+ group for the cationic diamines and polyamines.

Preferred ethoxylated cationic diamines have the formula:

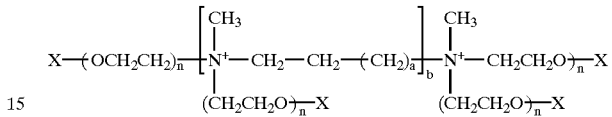

wherein X and n are defined as before, a is from 0 to 20, preferably from 0 to 4 (e.g. ethylene, propylene, hexamethylene) b is 1 or 0. For preferred cationic monoamines (b=0), n is preferably at least about 16, with a typical range of from about 20 to about 35. For preferred cationic diamines (b=1), n is at least about 12 with a typical range of from about 12 to about 42.

Optional Ingredients

The composition herein may comprise other optional ingredients, such as those selected from the group consisting of building agent, filler agent, enzymes, suds suppressor or combinations thereof. The composition herein may also comprise optional ingredients selected from the group consisting of bleaching agent, chelating agent, brightener or combinations thereof, although it is preferred that optional ingredients selected from the group consisting of bleaching agent, chelating agent, brightener or combinations thereof are not deliberately added to the composition herein and that the composition herein is free of bleaching agent, chelating agent, or brightener, since it is believed that the presence of these optional ingredients in the composition herein reduce the colour care benefit provided by said composition. These optional ingredients are described in more detail herein.

Polyethylene/propylene Glycols

The composition herein may comprise polyethylene and/or propylene glycol, particularly those of molecular weight 1000–10000, more particularly 2000 to 8000 and most preferably about 4000.

Building Agent

The composition herein preferably comprises (by weight) from 1% to 30%, more preferably from 2%, or from 3%, or from 4%, to 25%, or to 20%, or to 15%, or to 10%, or to 8% building agent. If the composition herein comprises a dye auxiliary agent, which is an organic acid especially a carboxylic acid such as citrate, which can act as a building agent in addition as a dye auxiliary agent, then said composition preferably comprises no building agent or a very low level of building agent such as an amount of building agent less than 6% by weight, preferably less than 1% by weight. Preferably the building agent is not an organic acid or a salt thereof and the weight ratio of dye auxiliary agent to said building agent is from 2:1 to 100:1, more preferably from 3:1 to 75:1, more preferably from 5:1 to 50:1, more preferably from 5:1 to 20:1, most preferably from 6:1 to 10:1. Preferably the building agent comprises a water-insoluble or partially water-soluble building agent, although the building agent may comprise a water-soluble building agent, or a combination of a water-insoluble or partially water-soluble building agent and a water-soluble building agent. Preferably the building agent comprises an aluminosilicate, such as zeolite A.

Water-insoluble or Partially Water-soluble Building Agent

The composition herein may comprise water-insoluble or partially water-soluble building agent. Examples of largely water insoluble building agents include the sodium aluminosilicates. Suitable aluminosilicate zeolites have the unit cell formula $$Na_z[(AlO_2)_z(SiO_2)_y]\cdot xH_2O$$

wherein z and y are at least 6; the molar ratio of z to y is from 1.0 to 0.5 and x is at least 5, preferably from 7.5 to 276, more preferably from 10 to 264.

The aluminosilicate material is in hydrated form and is preferably crystalline, containing from 10% to 28%, more preferably from 18% to 22% water in bound form. The aluminosilicate zeolites can be naturally occurring materials, but are preferably synthetically derived. Synthetic crystalline aluminosilicate ion exchange materials are available under the designations Zeolite A, Zeolite B, Zeolite P, Zeolite X, Zeolite HS and mixtures thereof. Zeolite A has the formula:

$$Na_{12}[(AlO_2)_{12}(SiO_2)_{12}]\cdot xH_2O$$

wherein x is from 20 to 30, especially 27. Zeolite X has the formula $Na_{86}[(AlO_2)_{86}(SiO_2)_{106}]\cdot 276\ H_2O$.

Preferred crystalline layered silicates for use herein have the general formula:

$$NaMSi_xO_{2x+1}\cdot yH_2O$$

wherein M is sodium or hydrogen, x is a number from 1.9 to 4 and y is a number from 0 to 20.

Crystalline layered sodium silicates of this type are disclosed in EP-A-0164514 and methods for their preparation are disclosed in DE-A-3417649 and DE-A-3742043. Herein, x in the general formula above preferably has a value of 2, 3 or 4 and is preferably 2. The most preferred material is $\delta$-$Na_2Si_2O_5$, available from Hoechst AG as NaSKS-6.

Water-soluble Building Agent

The composition herein may comprise a water-soluble building agent. Preferably, the water-soluble building agent comprises an alkali or earth alkali metal salt of phosphate. Suitable examples of a water-soluble phosphate building agents are the alkali metal tripolyphosphates, sodium, potassium and ammonium pyrophosphate, sodium and potassium and ammonium pyrophosphate, sodium and potassium orthophosphate, sodium polymeta/phosphate in which the degree of polymerisation ranges from about 6 to 21, and salts of phytic acid. The water-soluble building agent may also comprise a borate building agent or a building agent containing borate-forming material that can produce borate under storage or wash conditions.

Enzyme

The composition herein preferably comprises an enzyme or enzymes. Preferred additional enzymatic materials include the commercially available lipases, cutinases, amylases, neutral and alkaline proteases, esterases, cellulases, pectinases, lactases and peroxidases conventionally incorporated into detergent compositions. Suitable enzymes are discussed in U.S. Pat. Nos. 3,519,570 and 3,533,139.

Preferred commercially available protease enzymes include those sold under the tradenames Alcalase, Savinase, Primase, Durazym, and Esperase by Novo Industries A/S (Denmark), those sold under the tradename Maxatase, Maxacal and Maxapem by Gist-Brocades, those sold by Genencor International, and those sold under the tradename Opticlean and Optimase by Solvay Enzymes. Protease enzyme may be incorporated into the compositions in accordance with the invention at a level of from 0.0001% to 4% active enzyme by weight of the composition.

Preferred amylases include, for example, $\alpha$-amylases obtained from a special strain of B licheniformis, described in more detail in GB-1,269,839 (Novo). Preferred commercially available amylases include for example, those sold under the tradename Rapidase by Gist-Brocades, and those sold under the tradename Termamyl and BAN by Novo Industries A/S. Amylase enzyme may be incorporated into the composition in accordance with the invention at a level of from 0.0001% to 2% active enzyme by weight of the composition.

Lipolytic enzyme may be present at levels of active lipolytic enzyme of from 0.0001% to 10% by weight of the particle, preferably 0.001% to 3% by weight of the composition, most preferably from 0.001% to 0.5% by weight of the compositions. The lipase may be fungal or bacterial in origin being obtained, for example, from a lipase producing strain of *Humicola sp., Thermomyces sp.* or *Pseudomonas sp.* including *Pseudomonas pseudoalcaligenes* or *Pseudomas fluorescens*. Lipase from chemically or genetically modified mutants of these strains are also useful herein. A preferred lipase is derived from *Pseudomonas pseudoalcaligenes*, which is described in Granted European Patent, EP-B-0218272. Another preferred lipase herein is obtained by cloning the gene from *Humicola lanuginosa* and expressing the gene in *Aspergillus oryza*, as host, as described in European Patent Application, EP-A-0258 068, which is commercially available from Novo Industri A/S, Bagsvaerd, Denmark, under the trade name Lipolase. This lipase is also described in U.S. Pat. No. 4,810,414, Huge-Jensen et al, issued Mar. 7, 1989.

Suds Suppresser

The composition herein may comprise a suds suppresser, although it may not always be necessary to include a suds suppressor in the composition herein. It may be preferred that the composition herein comprises 0.005% to 0.5% by weight a suds suppresser. Preferably the suds suppresser is either a soap, paraffin, wax, suds suppressing silicone or any combination thereof, more preferably suds suppressing silicone.

Suitable suds suppressers for use herein may comprise essentially any known antifoam compound, including, for example silicone antifoam compounds and 2-alkyl alcanol antifoam compounds. By antifoam compound it is meant herein any compound or mixtures of compounds which act such as to depress the foaming or sudsing produced by a solution of a detergent composition, particularly in the presence of agitation of that solution. Particularly preferred antifoam compounds for use herein are silicone antifoam compounds defined herein as any antifoam compound including a silicone component. Such silicone antifoam compounds also typically contain a silica component. The term "silicone" as used herein, and in general throughout the industry, encompasses a variety of relatively high molecular weight polymers containing siloxane units and hydrocarbyl group of various types. Preferred silicone antifoam compounds are the siloxanes, particularly the polydimethylsiloxanes having trimethylsilyl end blocking units. Other suitable antifoam compounds include the monocarboxylic fatty acids and soluble salts thereof. These materials are described in U.S. Pat. No. 2,954,347, issued Sep. 27, 1960 to Wayne St. John. The monocarboxylic fatty acids, and salts thereof, for use as suds suppresser typically have hydrocarbyl chains of 10 to 24 carbon atoms, preferably 12 to 18 carbon atoms. Suitable salts include the alkali metal salts such as sodium, potassium, and lithium salts, and ammonium and alkanolammonium salts. Other suitable antifoam compounds include, for example, high molecular weight fatty esters (e.g. fatty acid triglycerides), fatty acid esters of monovalent alcohols, aliphatic $C_{18}$–$C_{40}$ ketones (e.g. stearone).

A preferred particulate suds suppressing system is described in EP-A-0210731 and comprises a silicone antifoam compound and an organic carrier material having a melting point in the range 50° C. to 85° C., wherein the organic carrier material comprises a monoester of glycerol and a fatty acid having a carbon chain containing from 12 to 20 carbon atoms. EP-A-0210721 discloses other preferred particulate suds suppressing systems wherein the organic carrier material is a fatty acid or alcohol having a carbon chain containing from 12 to 20 carbon atoms, or a mixture thereof, with a melting point of from 45° C. to 80° C.

Flocculating Agent

The composition herein may comprise a flocculating agent, suitable flocculating agents are organic polymeric clay flocculating agents such as those described in EP-A-299,575 and EP-A-313,146.

Fabric Softening Agents

The composition herein may comprise a fabric softening agent. can also be. Suitable fabric softening agents are cationic fabric softening agents such as water insoluble tertiary amines or dilong chain amide materials as described in GB-A-1 514 276 and EP-B-0 011 340.

Bleaching Agent

The composition herein is preferably free of bleach and comprises no bleaching agent, although in certain circumstances the composition herein may comprise a bleaching agent. Typical bleaching agents which may be used herein include sources of percarbonate and perborate, and alkyl percarboxylic acid precursors such as sodium 3,5,5-trimethyl hexanoyloxybenzene sulphonate (iso-NOBS), sodium nonanoyloxybenzene sulphonate (NOBS), sodium acetoxybenzene sulphonate (ABS) and pentaacetyl glucose.

Other Optional Ingredients

Other optional ingredients suitable for use herein include perfumes and filler salts, with sodium sulphate being a preferred filler salt.

Preferably, the composition herein comprises (by weight) from 10%, or from 15%, or from 20%, to 50%, or 40%, or 35% buffer agent. Preferably, the composition herein comprises an amount of buffer agent which, when said composition is used in solution during the washing cycle, the pH of said solution is from 6 to 12, preferably from 8 to 11. A preferred buffer agent is carbonate or bicarbonate, especially sodium carbonate, sodium bicarbonate, or combination thereof.

Preferably, the composition herein comprises (by weight) from 0.01% to 10%, preferably from 0.1% to 2% perfume. The perfume for use herein may be a spray-on perfume, an encapsulated perfume or a combination thereof. A typical perfume for use herein is described in U.S. patent application Ser. No. 99/15666.

Composition

The composition herein is preferably in solid form, e.g. in the form of a tablet, although liquid, gel or paste forms of the composition herein can be used herein. Preferably, the solid composition herein is in the form of a granular composition, for example including agglomerates, extradites, spray dried particles, or combinations thereof. The solid composition herein preferably has a bulk density of from 300 g/liter to 1000 g/liter, preferably from 400 g/liter to 850 g/liter.

Pouched Composition

Preferably, the composition herein is at least partially enclosed by a water-soluble film, preferably completely enclosed by a water-soluble film to form a water-soluble pouch. Preferably the water-soluble pouch is formed in such a manner so that the composition herein is prevented from contacting anything outside of the water-soluble pouch until the water-soluble film dissolves and releases the ingredients, including the dye and dye auxiliary agent, from the pouch.

The water-soluble film has a solubility of at least 50%, preferably at least 75% or even at least 95%, as measured by the method set out hereinafter using a glass-filter with a maximum pore size of 20 microns, namely:

Gravimetric method for determining water-solubility of the water-soluble film:

50 grams±0.1 gram of water-soluble film material is added in a 400 ml beaker, whereof the weight has been determined, and 245 ml±1 ml of distilled water is added. This is stirred vigorously on magnetic stirrer set at 600 rpm, for 30 minutes. Then, the mixture is filtered through a folded qualitative sintered-glass filter with the pore sizes as defined above (max. 20 or 50 micron). The water is dried off from the collected filtrate by any conventional method, and the weight of the remaining material is determined (which is the dissolved or dispersed fraction). Then, the % solubility can be calculated.

Preferred water-soluble films suitable for use herein are polymeric materials, preferably polymers which are formed into a film or sheet. The film can for example be obtained by casting, blow-moulding, extrusion or blow extrusion of the polymer material, as known in the art.

Preferred polymer copolymers or derivatives thereof are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferably the polymer is selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, most preferably polyvinyl alcohols, polyvinyl alcohol copolymers and hydroxypropyl methyl cellulose (HPMC).

The polymer can have any weight average molecular weight, preferably from 1000 to 1000000, or even from 10000 to 300000 or even from 15000 to 200000 or even from 20000 to 150000.

Mixtures of polymers can also be used. This may in particular be beneficial to control the mechanical and/or dissolution properties of the pouch, depending on the application thereof and the required needs. For example, it may be preferred that a mixture of polymers is present in the material of the compartment, whereby one polymer material has a higher water-solubility than another polymer material, and/or one polymer material has a higher mechanical strength than another polymer material. It may be preferred that a mixture of polymers is used, having different weight average molecular weights, for example a mixture of PVA or a copolymer thereof of a weight average molecular weight of from 10000 to 40000, preferably around 20000, and of PVA or copolymer thereof, with a weight average molecular weight of from 100000 to 300000, preferably 150000.

Also useful are polymer blend compositions, for example comprising hydrolytically degradable and water-soluble polymer blend such as polylactide and polyvinyl alcohol, achieved by the mixing of polylactide and polyvinyl alcohol, typically comprising 1–35% by weight polylactide and approximately from 65% to 99% by weight polyvinyl alcohol, if the material is to be water-dispersible, or water-soluble. It may be preferred that the polymer present in the film is from 60% to 98% hydrolysed, preferably 80% to 90%, to improve the dissolution of the material. The film herein may comprise other additive ingredients than the polymer or polymer material. For example, it may be beneficial to add plasticisers, for example glycerol, ethylene glycol, diethyleneglycol, propylene glycol, sorbitol and mixtures thereof, additional water, disintegrating aids.

Suitable examples of commercially available water-soluble films include polyvinyl alcohol and partially hydrolysed polyvinyl acetate, alginates, cellulose ethers such as carboxymethylcellulose and methylcellulose, polyethylene oxide, polyacrylates and combinations thereof. Most preferred are films which comprises PVA polymers and have similar properties to films that are known under the trade reference M8630, as sold by Chris-Craft Industrial Products of Gary, Ind., US.

Process for Preparing the Composition

The composition of the invention can be made by a variety of methods, including dry-mixing, extruding, co-compacting and agglomerating of the various compounds comprised in the composition. Preferably, the composition herein is prepared by a process comprising the steps; (a) premixing a fabric substantive dye and a dye auxiliary agent to form a dye premix; and (b) mixing surfactant with the dye premix. Other ingredients can be premixed with the dye and dye auxiliary agent during the premixing step (a), these ingredients may also include some but not all of the surfactant, although preferably only the dye and dye auxiliary agent are premixed during the premixing step (a).

Preferably, the dye and dye auxiliary agent are present in the composition herein as preformed particles such as co-compacted particles or agglomerates. The dye and dye auxiliary agent can be present in different separate preformed particles or can be present in the same preformed particle, preferably the dye and dye auxiliary agent are present in the same co-compacted particle. The Inventors have found that the presence of water in a preformed particle comprising dye and dye auxiliary agent, interacts with said dye and said dye auxiliary agent and decreases the colour care benefit provided by the composition. Therefore, preferably said preformed particle is anhydrous, and preferably comprises (by weight of said preformed particle) less than 10%, more preferably less than 8%, more preferably less than 5%, more preferably less than 3%, more preferably less than 2%, more preferably less than 1% chemically free water.

Method of Use

The composition herein can be used to dye and wash fabrics. The composition can be used to change the colour of a fabric, and thus can act as a fabric dying composition for example to dye a yellow fabric blue. The composition herein can also be used to refresh or enhance the colour of a fabric, and thus can be used for example to refresh a faded/worn blue coloured fabric so that the faded blue colour is returned to a blue colour. The composition herein can also be used to maintain the colour of a fabric, for example, the composition herein can be used as a detergent composition and can be used to wash fabrics, and during the washing process the colour of the fabric does not fade.

Preferably an adequate amount of composition is dispensed into a solution. By an adequate amount of composition it is meant from 10 g to 300 g, preferably from 15 g to 200 g, more preferably from 15 g to 150 g, even more preferably from 40 g to 100 g, most preferably from 50 g to 80 g, of product dissolved or dispersed in a solution of volume from 0.01 to 100 liters, preferably 0.05 to 70 liters, more preferably 0.1 to 70 liters, even more preferably 0.12 to 67 liters, most preferably from 0.12 to 65 liters. The composition herein can be used a conventional detergent product and the amounts above are typical product dosages and wash solution volumes commonly employed in conventional laundry methods. Other laundry washing processes known in the art can also be used. Typically, the composition herein is added to the drum, or alternatively to the dispensing draw, of an automatic washing machine.

If the composition herein is at least partially enclosed by a water-soluble film to form a water-soluble pouch, then the water-soluble pouch can be prepared as single unit dose pouch that weighs from as little as 1 g up to 100 g, preferably from 5 g, or from 10 g, or from 15 g, or from 20 g, to 80 g, or to 70 g, or to 60 g, or to 50 g. Pouches that are either lighter or heavier than 1 g or 100 g respectively, can be used but are difficult and complex to manufacture and use. Preferably the pouches for use herein weigh from 20 g to 40 g, and two pouches are added to a typical wash load in an automatic washing machine and are used to maintain the colour of the fabric during the washing process. Three or more pouches can be added to a typical wash load, preferably a slightly reduced wash load, in an automatic washing machine and are used to refresh or enhance the colour of the fabric during the washing process.

Preferably, the composition herein is the only fabric treatment composition used in the fabric treating process. Although one or more other compositions can be used in combination with the composition herein during the fabric treatment process, such that composition herein, for example is used as a pre-treatment, main-treatment, post-treatment or a combination thereof during a washing process. The composition herein can be used in a process for dying a fabric surface comprising the step of contacting the composition herein to a fabric surface.

EXAMPLES

Abbreviations Used in Examples

In the compositions, the abbreviated component identifications have the following meanings:

| | |
|---|---|
| Dye | Drimarene navy K-BNN dye |
| Benzoate | Sodium benzoate |
| Citrate | Tri-sodium citrate dihydrate of activity 86.4% with a particle size distribution between 425 microns to 850 microns. |
| CxyEz | $C_{1x}$-$C_{1y}$ predominantly linear primary alcohol condensed with an average of z moles of ethylene oxide |
| QAS | $R_2.N^+(CH_3)_2(C_2H_4OH)$ with $R_2 = C_8$–$C_{14}$ |
| Zeolite A | Hydrated sodium aluminosilicate of formula $Na_{12}(AlO_2SiO_2)_{12}.27H_2O$ having a primary particle size in the range from 0.1 to 10 micrometers (weight expressed on an anhydrous basis) |
| Carbonate | Anhydrous sodium carbonate having 80% by volume of particles with a particle size from 50 microns to 150 microns with a volume median particle size of 100 microns |
| Sulphate | Anhydrous sodium sulfate |
| Protease | Proteolytic enzyme, having 3.3% by weight of active enzyme, sold by NOVO Industries A/S under the tradename Savinase |
| Cellulase | Cellulytic enzyme, having 0.23% by weight of active |

-continued

| | |
|---|---|
| | enzyme, sold by NOVO Industries A/S under the tradename Carezyme |
| Amylase | Amylolytic enzyme, having 1.6% by weight of active enzyme, sold by NOVO Industries A/S under the tradename Termamyl 120T |
| Lipase | Lipolytic enzyme, having 2.0% by weight of active enzyme, sold by NOVO Industries A/S under the tradename Lipolase |
| QEA | bis(($C_2H_5O$)($C_2H_4O$)$_n$)($CH_3$)—$N^+$—$C_6H_{12}$—$N^+$—($CH_3$)bis(($C_2H_5O$)—($C_2H_4O$))$_n$, wherein n = from 20 to 30 |
| Silicone antifoam | Polydimethylsiloxane foam controller with siloxane-oxyalkylene copolymer as dispersing agent with a ratio of said foam controller to said dispersing agent of 10:1 to 100:1 |

Example 1

The following compositions A to I are fabric treatment compositions according to the present invention:

| Ingredient | A | B | C | D | E | F | G | H | I |
|---|---|---|---|---|---|---|---|---|---|
| Drimarene navy K-BNN dye | 0.5 | 0.4 | 1 | 0.2 | 1 | 1 | 0.5 | 0.2 | 1 |
| Benzoate | 40 | | 35 | 45 | 5 | 38 | 30 | 45 | 20 |
| Citrate | | 45 | | | 20 | | | | |
| QEA | 2 | 3 | 4 | 3 | 3 | 1.5 | 3 | 5 | 6 |
| C24E7 | 8 | 7 | 9 | 10 | 8 | 7 | 9 | 8 | 10 |
| QAS | 1 | 1.5 | 0.5 | 2 | 1 | 1 | 1.5 | 0.5 | 2 |
| Zeolite A | 6 | 4 | 7 | 6 | 5 | 7 | 8 | 6 | 10 |
| Carbonate | 31 | 25 | 30 | 20 | 35 | 31 | 25 | 30 | 25 |
| Sulphate | | 3 | | | 6 | 10 | 20 | | 13 |
| Protease | 0.5 | 0.4 | 0.5 | 0.2 | 0.7 | 0.1 | 0.4 | 0.5 | 0.4 |
| Lipase | 0.3 | 0.4 | 0.4 | 0.5 | 0.2 | 0.5 | 0.4 | 0.1 | 0.4 |
| Amylase | 0.5 | 0.3 | 0.1 | 0.5 | 0.4 | 0.7 | 0.5 | 0.2 | 0.5 |
| Cellulase | 0.2 | 0.4 | 0.5 | 0.3 | 0.1 | 0.5 | 0.3 | 0.5 | 0.4 |
| Perfume | 0.8 | 0.7 | 1 | 0.9 | 1 | 0.6 | 0.5 | 1 | 0.9 |
| Acetate | 9 | 8 | 10 | 11 | 13 | | | 2 | 10 |
| Silicone antifoam | | 0.1 | | 0.3 | | 0.2 | | | |
| Balance (moisture and miscellaneous) | to 100 | to 100 | to 100 | to 100 | to 100 | to 100 | to 100 | to 100 | to 100 |

Example 2

0.5 g drimarene navy K-BNN dye and 40 g sodium benzoate are dry mixed together to form a free flowing dye premix. The dye premix is then compressed using a Lloyd material tester LR50K under a pressure of 21834kNm-2 to form a dye tablet. The dye tablet is then crushed to form dye particles having a particle size of from 10 micrometers to 1000 micrometers, having a mean particle size of 300 micrometers. The dye particles are then added to base composition comprising 10 g surfactant, 30 g sodium carbonate, 2 g enzyme, 1 g perfume, 10 g acetate, 6 g zeolite A to form a composition in accord with the present invention.

Example 3

0.5 g drimarene navy K-BNN dye and 40 g sodium benzoate are dispersed in 2 g bis(($C_2H_5O$)($C_2H_4O$)$_{30}$)($CH_3$)—$N^+$—$C_6H_{12}$—$N^+$—($CH_3$) bis(($C_2H_5O$)-($C_2H_4O$))$_{30}$, at 50° C. to form a dye dispersion. The dye dispersion is extruded using a twin screw extruder to form extruded material. The extruded material is cut to form dye particles having a particle size of form 10 micrometers to 1000 micrometers, having a mean particle size of 300 micrometers. The dye particles are added to a base composition comprising 10 g surfactant, 30 g sodium carbonate, 2 g enzyme, 1 g perfume, 10 g acetate, 6 g zeolite A to form a composition in accord with the present invention.

Example 4

A wash load consisting of 2 kg black and blue fabric garments was loaded into an automatic washing machine. 75 g composition A from example 1 was added to a dispensing device which was then placed in the drum of said automatic washing machine. The washing load was washed under standard European washing conditions (for 45 minute wash time, 3 times 10, minute rinse time, at 40° C.) using composition A of example 1.

What is claimed is:

1. A fabric treatment composition comprising at least 3% surfactant, from 0.01% to 3% fabric substantive dye, and at least 10% dye auxiliary agent, by weight of said fabric treatment composition; wherein said dye auxiliary agent comprises a carboxylic acid or salt thereof.

2. A fabric treatment composition according to claim 1, wherein said fabric treatment composition comprises from 0.01% to 1% fabric substantive dye, by weight of said fabric treatment composition.

3. A fabric treatment composition according to claim 2, wherein said fabric treatment composition comprises from 0.01% to 0.7% fabric substantive dye, by weight of said fabric treatment composition.

4. A fabric treatment composition according to claim 1, wherein said fabric substantive dye is a reactive dye comprising a chromophore group, a linking group, and a leaving group.

5. A fabric treatment composition according to claim 4, wherein said linking group is a triazine group or a pyrimidine group, and/or said leaving group is a halide atom.

6. A fabric treatment composition according to claim 5, wherein said leaving group is a chlorine atom.

7. A fabric treatment composition according to claim 5, wherein said leaving group is a fluorine atom.

8. A fabric treatment composition according to claim 1, wherein said fabric substantive dye is a DRIMARENE dye.

9. A fabric treatment composition according to claim 1, wherein said fabric treatment composition comprises from 20% to 70% dye auxiliary agent, by weight of the fabric treatment composition.

10. A fabric treatment composition according to claim 9, wherein said fabric treatment composition comprises from 30% to 30% dye auxiliary agent, by weight of the fabric treatment composition.

11. A fabric treatment composition according to claim 1, wherein said dye auxiliary agent has a molecular weight of less than 1000.

12. A fabric treatment composition according to claim 11, wherein said dye auxiliary agent comprises an aromatic carboxylic acid or salt thereof.

13. A fabric treatment composition according to claim 11, wherein said dye auxiliary agent comprises a benzoic acid or salt thereof, a substituted benzoic acid and salt thereof, or a combination thereof.

14. A fabric treatment composition according to claim 1, wherein:
   (a) said fabric treatment composition is free of anionic surfactant; and/or
   (b) said surfactant comprises a nonionic surfactant, a cationic surfactant or a mixture thereof.

15. A fabric treatment composition according to claim 14, wherein said surfactant comprises a mixture of nonionic surfactant and cationic surfactant, wherein a weight ratio of nonionic surfactant to cationic surfactant is from 5:1 to 20:1.

16. A fabric treatment composition according to claim 1, wherein said fabric treatment composition comprises from 0.1% to 10% cationic polymeric material, by weight of said fabric treatment composition.

17. A fabric treatment composition according to claim 1, wherein said fabric substantive dye and said dye agent are present in said fabric treatment composition in the form of a preformed particle.

18. A fabric treatment composition according to claim 1, wherein said fabric treatment composition is at least partially enclosed by a water-soluble film.

19. A process of preparing a fabric treatment composition according to claim 1, comprising the steps of:
   (a) premixing a fabric substantive dye and a dye auxiliary agent to form a dye premix; and
   (b) mixing a surfactant with said dye premix;
   wherein said dye auxiliary agent comprises a carboxylic acid or salt thereof.

20. A process of dying a fabric surface comprising the step of contacting said fabric surface with a fabric treatment composition according to claim 1.

* * * * *

UNITED STATES PATENT AND TRADEMARK OFFICE
CERTIFICATE OF CORRECTION

PATENT NO. : 6,726,731 B2
DATED : June 28, 2001
INVENTOR(S) : Robert Michael Pettifer It is certified that error appears in the above-identified patent and that said Letters Patent is hereby corrected as shown below:

Column 19,
Line 1, please replace "30%" with -- 50% --.

Signed and Sealed this

Twenty-fifth Day of October, 2005

JON W. DUDAS
*Director of the United States Patent and Trademark Office*